United States Patent [19]

Louiday

[11] Patent Number: 4,989,228
[45] Date of Patent: Jan. 29, 1991

[54] RADIOLOGICAL EXAMINATION DEVICE

[75] Inventor: André E. Louiday, Le Pacq, France

[73] Assignee: U. S. Philips Corporation, New York, N.Y.

[21] Appl. No.: 360,959

[22] Filed: Jun. 2, 1989

[30] Foreign Application Priority Data

Jun. 10, 1988 [FR] France ............................ 88 07776

[51] Int. Cl.⁵ .............................................. H05G 1/02
[52] U.S. Cl. ..................................... 378/196; 378/197
[58] Field of Search ......................... 378/195, 196, 197

[56] References Cited

U.S. PATENT DOCUMENTS 4,149,078  4/1979  Hahn et al. ......................... 378/195
4,408,341  10/1983  Christiansen ....................... 378/196

FOREIGN PATENT DOCUMENTS 2922960  12/1979  Fed. Rep. of Germany .
2591466  6/1987  France .

Primary Examiner—Craig E. Church
Attorney, Agent, or Firm—William Squire

[57] ABSTRACT

A radiological examination device, comprising a base (1) which supports a patient table (2), a motor block (10) comprising a drive shaft (14) whose longitudinal axis extends transversely of the patient table, and displacement means which are linked to the motor block and which are composed of a motor block which is displaceable on a linear support (11) of the patient table, a drive chain which is rigidly connected to the motor block (10) and is closed thereon, the chain imparting, upon displacement of the motor block on its linear support, either a translatory or a rotary movement to a column which supports an X-ray imaging system.

6 Claims, 2 Drawing Sheets

RADIOLOGICAL EXAMINATION DEVICE

BACKGROUND OF THE INVENTION

1. Field of the Invention

The invention relates to a radiological examination device, comprising a base which supports a parallelepiped patient table, a motor block provided with a horizontal drive shaft whose longitudinal axis extends transversely of the patient table, and displacement means which are linked to the motor block.

2. Prior Art

A radiological examination device of this kind is known from French patent application No. 2,591,466. The cited Patent Application describes a radiological examination device which comprises a patient table which is displaceable in the longitudinal direction, a base which is provided with supporting means and displacement means, and a motor which is mounted on the base and which cooperates with the displacement means in order to displace the table with respect to the base. Displacement takes place under the influence of the motor which is integral with the base and whose rotary movement is transformed into a linear movement which is transferred to the table via a system of rollers, pulleys and belts. The motor shaft is rotated and drives, via toothed pinions, belts whose extremities are secured to the table to be displaced. The belts are guided on different pulleys and their displacement causes the displacement of the patient table. The various pulleys and rollers are supported by supporting shafts which are integral with the base.

One of the drawbacks of the examination device consists in the distribution of the various pulleys and rollers of the displacement means, resulting in a large base dimension, in the direction parallel to the longitudinal axis of the table. This large dimension of the base is objectionable, notably in the case of examination devices where easy access to the patient is necessary from both sides of the patient table. Moreover, the multitude of pulleys and rollers substantially increases the costs of the examination device.

Another drawback consists in that the displacement means is capable of producing a linear movement, only.

SUMMARY OF THE INVENTION

It is the object of the invention to provide a radiological examination device in which a displacement means can alternatively produce a translatory movement or a rotary movement in a simple manner for displacement of a column with respect to a table, which column supports a comparatively heavy imaging system which comprises an X-ray source and a serialographic unit.

The invention is characterized in that the displacement means comprises a motor block which is displaceable on a linear support in the longitudinal direction of the patient table, a drive chain which is rigidly connected to the motor block and which is closed thereon, the chain driving, upon displacement of the motor block on its linear support, a column either in a translatory mode on a longitudinal sliding rail of the patient table or in a rotary mode about a shaft of the column, horizontally and transversely of the table, supported by a mobile part of the sliding rail, the column supporting an imaging system composed of an X-ray source and a serialographic unit.

The alternating longitudinal and rotary movement are realized because the chain is formed by a loop which is closed on the motor block, the column being alternately blocked either in rotation or in translation.

Preferably, the motor block is coupled to a balancing weight and drives the balancing weight in opposition to the column with respect to the transversal symmetry plane of the patient table. The balancing weight enables partial compensation, via the displacement of the motor block, of the mass of the column and the imaging system. The motor block is displaced on a linear support of the patient table in opposition to the translatory movement of the column supporting the imaging system. This enables balancing, on both sides of a central supporting axis of the patient table, of the mass of the column comprising an imaging system and the mass of the motor block comprising the balancing weight. The mass of the motor block is partly used for the overall balancing mass.

In a preferred embodiment in accordance with the invention, the rotation of the column is provided by a ring portion on which the drive chain is guided and which ring is supported by a carriage and linked to the column by a drive pinion which is arranged between the column shaft and the X-ray source of the imaging system. The drive pinion between the column axis and the X-ray shaft of the imaging system, having a substantial mass, enables easy rotary displacement of the column. The motor exerts a comparatively reduced couple and may have a lower rated power.

In one embodiment of the invention the rotary and translatory displacements of the column are provided by a double brake which alternately inhibits either the rotation of the column for its translatory displacement, or the translation of the column for its rotary displacement.

Each of the two movements is produced by a motor which is connected to a brake which alternately blocks either the rotation of the column about its shaft or the translation of the carriage with respect to the patient table.

BRIEF DESCRIPTION OF THE DRAWING

The invention will be described in detail hereinafter, by way of example, with reference to the accompanying drawings wherein.

DETAILED DESCRIPTION OF THE PREFERRED EMBODIMENTS

Figure 1:
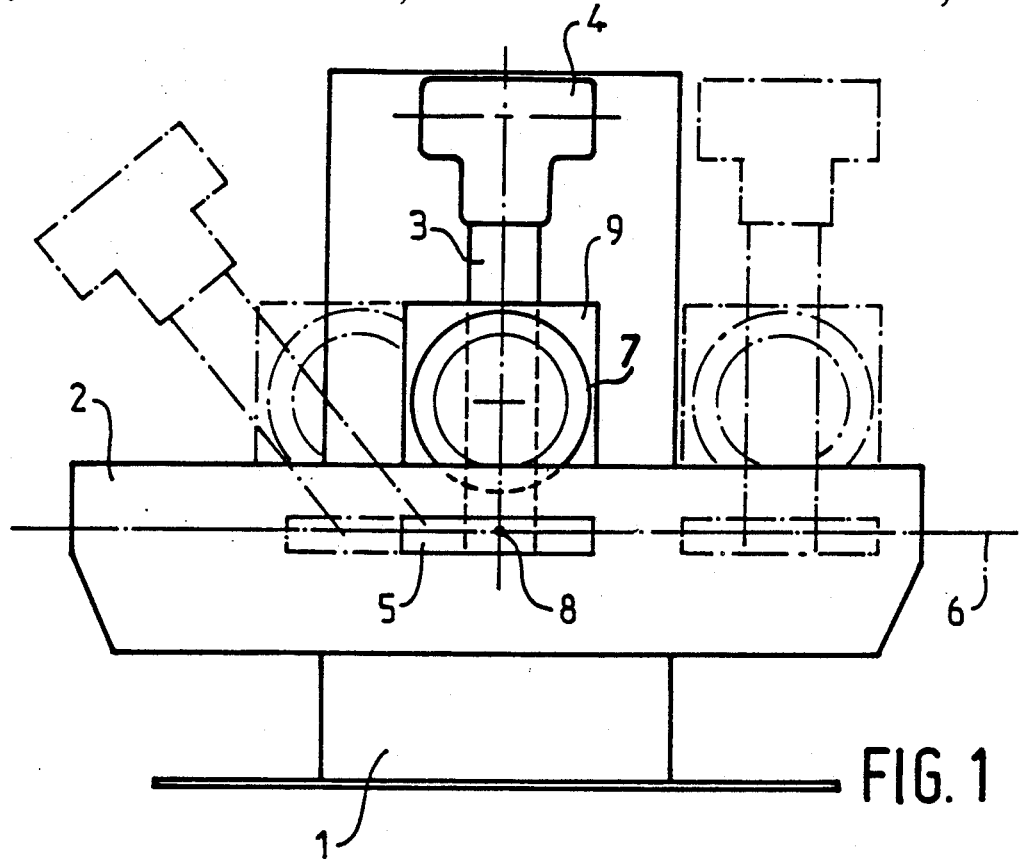
FIG. 1 shows a radiological examination device in accordance with the invention.

FIG. 1 shows a radiological examination device which comprises a base 1 which supports a tiltable patient table 2 and a mobile column 3 which itself supports at one of its ends an X-ray source 4, above the table, and at its other end a serialographic unit 5 which is arranged in the patient table 2.

The patient table 2 which is tiltable about a central supporting shaft supports a longitudinal sliding rail (not shown in the drawing) on which there is slidable, along a horizontal axis 6, a sliding block which supports a shaft 8 of the column which extends horizontally and transversely of the patient table 2, enabling rotation and tilting of the column 3.

The longitudinal displacement of the sliding block whereto the serialographic unit 5 is connected enables longitudinal displacement of the shaft of the column and hence a displacement of the serialographic unit 5 in the longitudinal direction of the patient table 2.

A carriage 9 is displaceable in the longitudinal direction of the patient table 2 and supports a ring 7 for the rotary motion of the column 3.

Figure 2:
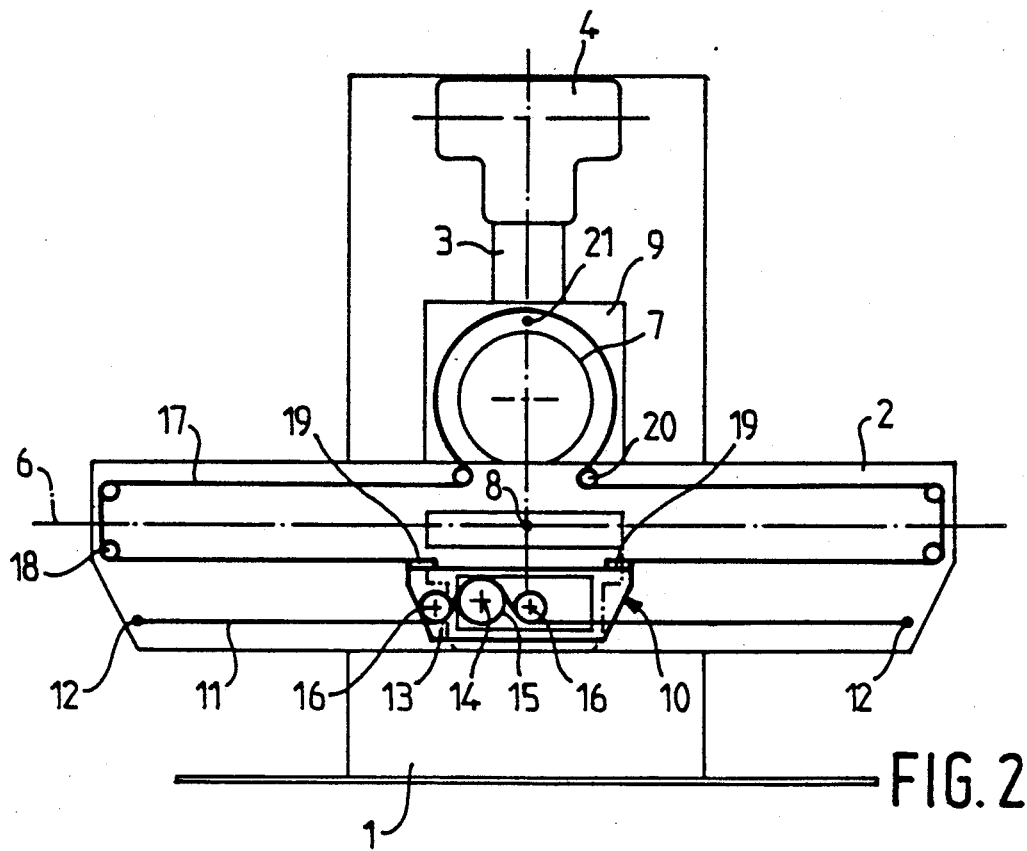
FIG. 2 shows a diagram illustrating the displacement means for the column supporting an imaging system.

FIG. 2 illustrates the displacement means for the column 3, said displacement means being composed of a motor block 10 which is displaceable on a linear support 11 which is secured to the patient table 2 by way of two of its extremities 12, parallel to the longitudinal axis 6 of the patient table 2. The motor block 10 is formed by a frame 13 which supports an electric motor and its transmission, the drive shaft 14 thereof extending horizontally and perpendicularly with respect to the longitudinal axis 6 of the patient table 2. The drive shaft 14 comprises a gearwheel 15 which is linked to the linear support 11 by way of guide gearwheels 16 mounted on the frame 13 in order to enable displacement of the motor block along the linear support 11. In the embodiment in accordance with the invention the linear support 11 is formed by a supporting chain which is engaged by the gearwheel 15 and the guide gearwheels 16. The linear support 11 of the motor block 10 may be, for example a rigid toothed rack. The motor block 10 also comprises, arranged in the frame 13, balancing weights which enable compensation for undesirable bearing forces exerted by the column 3 and the X-ray source 4 when they are arranged on both sides of a central supporting axis of the patient table.

On both sides of the frame 13 of the motor block 10 the two extremities of a drive chain 17 are secured in two anchoring points 19, which drive chain 17 forms a closed loop with the motor block 10 and engages on the one hand idle gearwheels 18 at the two extremities of the patient table and on the other hand around the toothed ring 7 of the carriage 9 via rollers 20 mounted on carriage 9.

The column 3 is linked to the ring 7 by a drive pinion 21. A double alternating brake (not shown in the drawings) provides either blocking of the column 3 by firmly locking ring 7 and the carriage 9, or blocking of the carriage by rigidly locking it to the patient table 2.

The radiological examination device operates as follows:

In a situation 1 as shown in FIG. 2, the motor block 10 and the carriage 9 are arranged on the transverse axis of the table and the examination device, the forces exerted by the assembly formed by the patient table 2, the motor block 10 and the column 3 then bear directly on the central supporting shaft of the patient table 2.

Figure 3A:
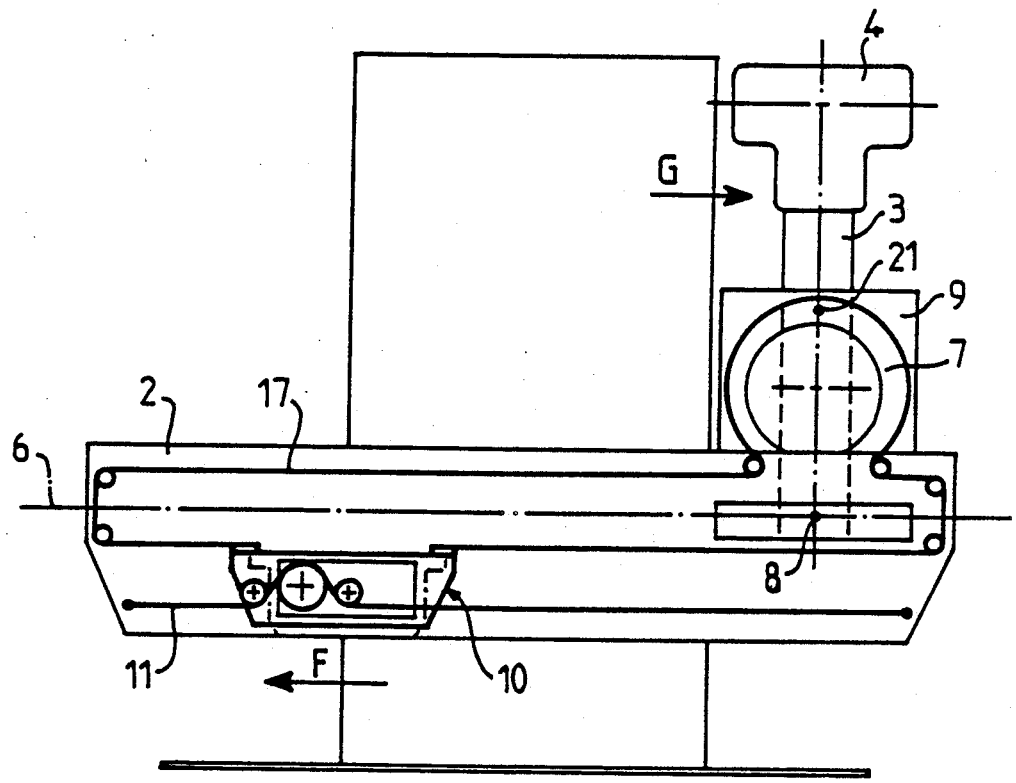
FIG. 3a shows a diagram illustrating the longitudinal displacement of the column.

In a situation 2 as shown in FIG. 3a, the double alternating brake rigidly locks the ring 7 and the carriage 9. The driving of the motor block 10 in the direction of the arrow F by rotation of the motor along the linear support 11, displaces via the drive chain 17, the carriage 9 as well as the column 3 in the direction of the arrow G, the longitudinal axis of the column 3 constantly extending in the same direction.

With respect to the central supporting shaft of the patient table 2 the motor block 10 is displaced in opposition to the carriage and the column, thus enabling the motor block 10, comprising a balancing weight, to compensate for the couple generated by the weight of the column with respect to the central supporting shaft of the patient table 2.

Figure 3B:
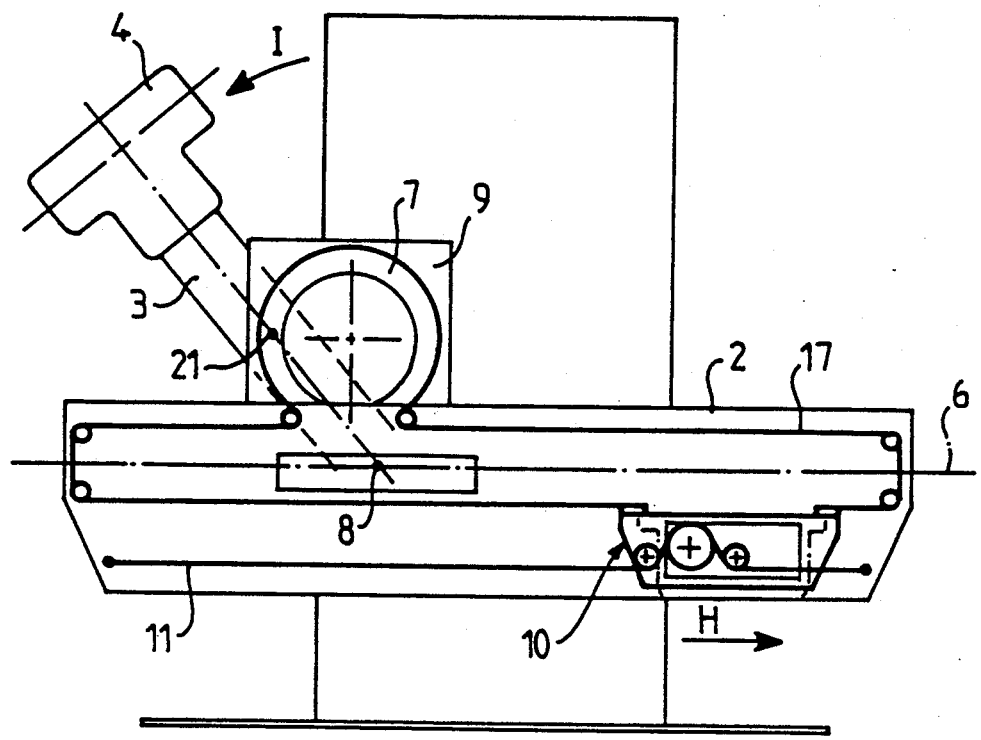
FIG. 3b shows a diagram illustrating the rotary displacement of the column.

In a situation 3 as shown in FIG. 3b, the double alternating brake rigidly locks the carriage 9 to the patient table 2, for example in a position as indicated in the Figure. The displacement of the motor block along the linear support 11 in the direction of the arrow H causes a rotation of the ring 7 via the drive chain 17. The rotation of the ring 7 enables inclination, in the direction of the arrow I, of the column 3 which is linked thereto via the drive pinion 21. The column is titled about the shaft 8 of the column. In this position the motor block, provided with its balancing weights, partly compensates for the mass of the column and the X-ray source.

The ring 7 and the position of the drive pinion 21 enable an attractive reduction of the rated power of the motor because the mechanical force produced by the drive chain and the motor block during inclination of the column is reduced by the lever arm formed by the distance separating the drive pinion 21 from the shaft 8 of the column.

What is claimed is:

1. A radiological examination device, comprising a base which supports a parallelepiped patient table having a longitudinal axis, said table including a longitudinal sliding rail having a mobile part, a motor block provided with a horizontal drive shaft whose longitudinal axis extends transversely of the patient table, a linear support for the motor block and displacement means which are linked to the motor block, characterized in that the displacement means comprises a motor block which is displaceable on said linear support in the longitudinal direction of the patient table, a drive chain which is secured to the motor block and which forms a closed loop therewith, said chain driving upon displacement of the motor block on its linear support, a column either in a translatory mode on the longitudinal sliding rail of the patient table, or in a rotary mode about a shaft of the column, horizontally and transversely of the table, supported by the mobile part of the sliding rail, the column supporting an imaging system composed of an X-ray source and a serialographic unit.

2. An examination device as claimed in claim 1, characterized in that the motor block is coupled to a balancing weight and drives the balancing weight in opposition to the column with respect to the transversal symmetry plane of the patient table.

3. An examination device as claimed in claim 1, characterized in that the rotation of the column is provided by a ring portion on which the drive chain is guided and which is supported by to a carriage and linked to the column by a drive pinion which is arranged between the column shaft and the X-ray source of the imaging system.

4. An examination device as claimed in claim 1, characterized in that the rotary and translatory displacements of the column are provided by a double brake which alternately inhibits either the rotation of the column for its translatory displacement, or the translation of the column for its rotary displacement.

5. An examination device as claimed in claim 2, characterized in that the rotation of the column is provided by a ring portion on which the drive chain is guided and which is supported by to a carriage and linked to the column by a drive pinion which is arranged between the column shaft and the X-ray source of the imaging system.

6. An examination device as claimed in claim 2, characterized in that the rotary and translatory displacements of the column are provided by a double brake which alternately inhibits either the rotation of the column for its translatory displacement, or the translation of the column for its rotary displacement.

* * * * *